United States Patent
Geebelen et al.

(10) Patent No.: US 10,762,623 B2
(45) Date of Patent: Sep. 1, 2020

(54) SYSTEM AND METHOD OF IMPROVING SURGICAL DEVICES USING CAPTURED IMAGES FOR EFFICIENT SURGICAL PLAN DEVELOPMENT

(71) Applicant: MATERIALISE N.V., Leuven (BE)

(72) Inventors: Benjamin Geebelen, Leuven (BE); Roel Wirix-Speetjens, Leuven (BE)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 15/525,231

(22) PCT Filed: Nov. 12, 2015

(86) PCT No.: PCT/US2015/060479
§ 371 (c)(1),
(2) Date: May 8, 2017

(87) PCT Pub. No.: WO2016/077646
PCT Pub. Date: May 19, 2016

(65) Prior Publication Data
US 2017/0337679 A1    Nov. 23, 2017

Related U.S. Application Data

(60) Provisional application No. 62/078,881, filed on Nov. 12, 2014.

(51) Int. Cl.
*G06T 7/00* (2017.01)
*G06T 7/10* (2017.01)
(Continued)

(52) U.S. Cl.
CPC ............ *G06T 7/0012* (2013.01); *A61B 34/10* (2016.02); *G06F 19/321* (2013.01);
(Continued)

(58) Field of Classification Search
CPC .............. A61B 34/10; A61B 2034/108; A61B 2034/102; A61B 34/25; G06T 7/0012;
(Continued)

(56) References Cited

U.S. PATENT DOCUMENTS

| 2012/0041446 A1* | 2/2012 | Wong ................. A61B 17/1703 606/96 |
| 2012/0093377 A1 | 4/2012 | Tsougarakis et al. |

(Continued)

FOREIGN PATENT DOCUMENTS

| JP | 2014-529314 A | 11/2014 |
| WO | 2010/148103 A1 | 12/2010 |

OTHER PUBLICATIONS

International Search Report and Written Opinion issued in corresponding International Application No. PCT/US2015/060479, dated Feb. 3, 2016, 8 pages.

(Continued)

*Primary Examiner* — Kenny A Cese
(74) *Attorney, Agent, or Firm* — Patterson + Sheridan, LLP (57) ABSTRACT

A two-step approach for image segmentation during the treatment planning process is disclosed. In a first step, an automatic segmentation method can be used to generate a first, provisional segmentation. The first, provisional segmentation may be generated using fast, but less accurate segmentation methods. The first provisional segmentation may be used to generate a default treatment plan for approval. Once the default treatment plan is approved, a more robust, second image segmentation may be performed. The second segmentation may be used to design patient-specific devices that can be used to deliver the patient-specific medical treatment.

18 Claims, 8 Drawing Sheets

(51) Int. Cl.
*G06T 7/11* (2017.01)
*G06T 7/13* (2017.01)
*G16H 50/20* (2018.01)
*G06F 19/00* (2018.01)
*G06T 7/136* (2017.01)
*G16H 30/40* (2018.01)
*A61B 34/10* (2016.01)
*G16H 50/50* (2018.01)
*G16H 20/40* (2018.01)

(52) U.S. Cl.
CPC ............ *G06F 19/3481* (2013.01); *G06T 7/10* (2017.01); *G06T 7/136* (2017.01); *G16H 20/40* (2018.01); *G16H 30/40* (2018.01); *G16H 50/20* (2018.01); *G16H 50/50* (2018.01); *G06T 7/11* (2017.01); *G06T 2207/10081* (2013.01); *G06T 2207/10088* (2013.01); *G06T 2207/10116* (2013.01); *G06T 2207/30008* (2013.01)

(58) Field of Classification Search
CPC .......... G06T 15/00; G06T 19/00; G06T 7/10; G06T 7/11; G06T 7/136; G06T 7/13; G06T 17/00; G06T 2207/30004; G06T 2207/30052; A61F 2/30942; G06F 17/50; G06F 19/3481; G06F 19/321; G16H 50/50; G16H 50/20; G16H 30/40; G16H 20/40
See application file for complete search history.

(56) References Cited

U.S. PATENT DOCUMENTS

| | | | |
|---|---|---|---|
| 2012/0130226 A1* | 5/2012 | Huizenga | A61B 5/055 600/411 |
| 2012/0230566 A1* | 9/2012 | Dean | A61B 34/10 382/131 |
| 2013/0211531 A1* | 8/2013 | Steines | A61F 2/3859 623/20.35 |
| 2013/0292870 A1* | 11/2013 | Roger | A61B 17/155 264/138 |
| 2014/0018948 A1* | 1/2014 | Metzger | A61F 2/5046 700/98 |
| 2014/0244220 A1 | 8/2014 | McKinnon et al. | |

OTHER PUBLICATIONS

Audenaert, E. et al., A custom-made guide for femoral component positioning in hip resurfacing arthroplasty: development and validation study, Computer Aided Surgery, vol. 16:6, Oct. 17, 2011, pp. 304-309.

Gomes, G.T. et al., Patient-Specific Modelling in Orthopedics: From Image to Surgery, Deformation Models, Jan. 1, 2013, vol. 4, pp. 109-129.

Van Parys, M. et al., 3D imaging and its applications in orthopedics: a state of play.

* cited by examiner

SYSTEM AND METHOD OF IMPROVING SURGICAL DEVICES USING CAPTURED IMAGES FOR EFFICIENT SURGICAL PLAN DEVELOPMENT

CROSS-REFERENCE TO RELATED APPLICATIONS

This application claims priority to U.S. Provisional Application No. 62/078,881, filed Nov. 12, 2014, the entire disclosure of which is hereby incorporated by reference.

BACKGROUND OF THE INVENTION

Field of the Invention

This application relates to surgery and surgical devices. More particularly, this application relates to a system and method of improving patient-specific surgery by more efficiently creating surgical plans using a two-step approach for image segmentation.

Description of the Related Technology

Currently, successfully carrying out patient-specific medical treatment typically requires that there be available three-dimensional ("3D") information about the relevant patient anatomy. This 3D information is usually extracted from medical images of the patient. These medical images may be CT images, MRI images, ultrasound images, or some other image modality. The medical images are converted into a 3D model using a process called segmentation. Although segmentation can be a manual process or an automatic process, automatic segmentation often leads to less accurate 3D models which are inadequate for planning patient-specific surgical procedures. Because automatic segmentation is not generally used, the planning time for a patient-specific surgical procedures can be quite long—often taking several weeks of coordination and input from various persons or teams involved in the planning. Improvements to the planning of patient-specific medical treatment are needed.

SUMMARY

In one embodiment, a method of delivering a patient-specific medical treatment to a patient is provided. The method may include acquiring image data of a patient anatomy and uploading image data to an automated segmentation portal. The method may further include receiving a default treatment plan from the automated segmentation portal, wherein the default treatment plan is generated based on first segmentation of the image data performed by the automated segmentation portal. The generated treatment plan may be approved, and the approved treatment plan may be transmitted to a service provider. The method may further include receiving a medical device from the service provider, wherein the medical device comprises at least one of a patient-matched medical device selected from a device library or a manufactured patient-specific medical device, wherein the medical device is based on a second segmentation of the image data, the second segmentation of the image data being more accurate than the first segmentation of the image data. The method may further include delivering the patient-specific treatment to the patient using the received medical device.

DETAILED DESCRIPTION OF CERTAIN INVENTIVE EMBODIMENTS

Embodiments disclosed herein relate to systems and methods which allow for a more efficient process of planning and delivering patient-specific medical treatment. In particular, the inventors have recognized certain unresolved inefficiencies in current processes, and have devised a two-step approach for image segmentation during the treatment planning process that significantly reduces these inefficiencies. In a first step, an automatic segmentation method can be used to generate a first, provisional segmentation. By utilizing an automatic segmentation method in the first instance, the need to involve a third party (such as a 3D segmentation professional) in the initial treatment planning is eliminated. Instead, the care provider can perform this aspect of the planning process without assistance. The quality and accuracy of such an automatic segmentation may be sufficient for designing patient-specific devices, but it is generally good enough for treatment planning. In a second step, once the treatment planning has been approved, the segmentation can be manually fine-tuned, or, alternatively, completed using a more computationally intensive automatic segmentation method. Thus, during the second step, a service provider is able to improve the quality and accuracy of the segmentation until it is good enough for device design.

Figure 1:
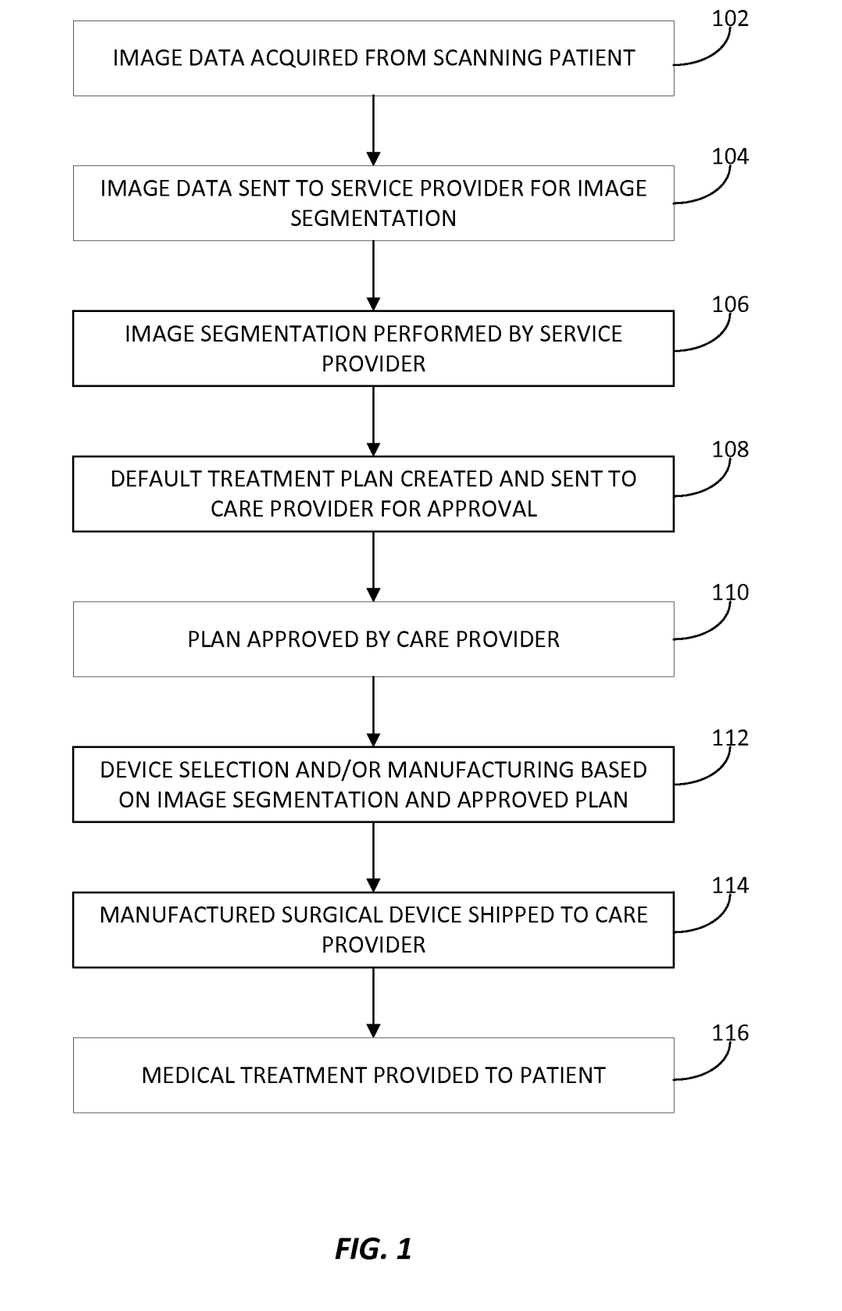
FIG. 1 is a flow chart illustrating a conventional method for planning a patient-specific medical treatment.

FIG. 1 is a flow chart illustrating a conventional method for planning a patient-specific medical treatment. In general, these patient-specific medical treatments rely on the availability of three-dimensional information about the relevant patient anatomy. The process begins at block 102, where medical image data regarding the relevant anatomy of the patient is acquired. The medical image data may be acquired using various different imaging technologies. These imaging technologies may include x-ray, MRI, CT scans, ultrasound, and the like. Once the image data has been acquired, the process then moves to block 104. There, the acquired image data may be sent to a service provider for image segmentation. A service provider, as used herein, refers to a person or entity who provides services relating to 3D device design and which enable a care provider to deliver patient-specific medical services to a patient. A service provider may include a medical device manufacturing company that designs and/or manufactures patient-specific medical devices. A service provider may also include a company or entity related to the care provider which is capable of generating and/or manufacturing patient-specific implants, instruments, and other devices suitable for delivering patient-specific care.

Once the image data has been sent to the service provider for image segmentation, the process then moves to block 106, where image segmentation is performed by the service provider. As discussed above, image segmentation converts the medical images into a virtual 3-D model, which can later be used to create a patient-specific device using additive manufacturing technologies. The process then moves to block 108, where the service provider also creates a default treatment plan. The default treatment plan can be an implant selection, a proposed implant position and/or orientation, a design of a patient-specific instrument, or some other plan for delivering the patient-specific treatment to the patient. The default treatment plan is transferred back to the care provider. Generally, the default treatment plan will rely heavily on the image data received in order to develop a default treatment plan that makes efficient use of patient-specific and/or patient-matched devices.

Next, at block 110, the care provider reviews the default treatment plan provided by the service provider. As part of its review, the care provider may adapt and/or fine-tune the treatment plan. Ultimately, the care provider will either approve the default plan (possibly as fine-tuned or adapted) or the care provider may reject the default plan. If the default plan is rejected, it is sent back to the service provider for a second design/approval round. Once the care provider is satisfied with the plan, the plan may be approved. Next, the process moves to block 112, where the plan is transferred back to the service provider and the service provider begins its preparation of the patient-specific medical treatment. This preparation may involve the design and manufacturing of anatomical models, patient-specific instruments, patient-specific implants, or the selection of patient-matched off-the-shelf devices for use in the patient treatment. Next, the process moves to block 114. There, the devices selected and/or manufactured by the service provider are shipped to the care provider. Once the care provider receives the manufactured and/or selected devices, the process then moves to block 116 where treatment is delivered to the patient by the care provider.

The inventors have recognized that this conventional process has a significant logistical drawback. Namely, there is a limited ability for care providers and services providers to coordinate the plan review in an efficient way. Care providers (such as orthopedic surgeons, for example) often have very busy and inflexible schedules that allow limited time for review. As a result, when service providers deliver preliminary/default plans to the care providers, the care providers often take several days, and even weeks to review, comment, revise, and/or approve the default plan. And, if the care provider determines that the plan requires modification, the same feedback loop must take place again, potentially adding several additional days and/or weeks of additional delay. The efficiency of the service provider may also suffer as a result of an inordinately long feedback loop. In particular, in its capacity planning, the service provider must account for a significant waiting period for the treatment plan approval.

Although the actual plan approval process can be quite short (sometimes requiring only 5 to 10 minutes of review), the lack of flexibility in the schedules of care providers often requires that the service provider build significant delays into the overall schedule in order to avoid having to adjust the schedule as the project unfolds. The end result of these lengthy feedback loops is that the delivery of patient care can be delayed for a significant amount of time. These delays can impact the quality of care because the patient is forced to wait for their patient-specific medical treatment. These delays may also impact the quality of care because the lead time needed to complete the patient-specific process can cause the patient and/or surgeon to avoid patient-specific options altogether. Although efforts have been made to avoid some of these logistical issues, none have proven satisfactory in the field. For example, care providers and service providers have made efforts to provide expedited treatment in certain cases. In these situations, the care provider makes an effort to approve the default plan as soon as it becomes available. However, in these cases, the service provider must make additional adjustments to its capacity planning so that the customary long lead times and the expedited lead times are both effectively managed.

Figure 2:
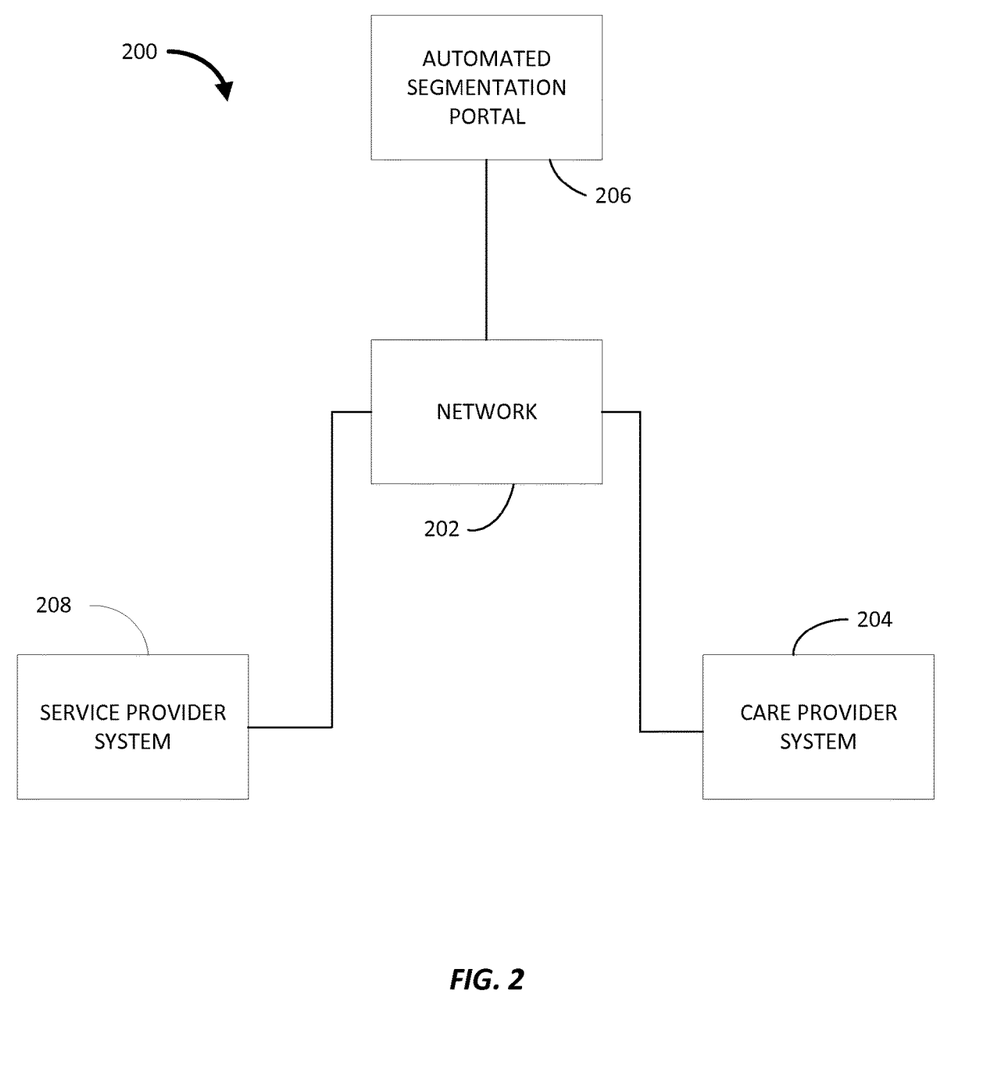
FIG. 2 is a block diagram illustrating a computer network environment suitable for carrying out one or more embodiments disclosed herein.

In recognizing these problems, the inventors have developed a two-step approach for image segmentation which can reduce and/or eliminate the lengthy feedback loops described above. This new two-step approach may be implemented in a computer network environment which allows for secure, electronic communication between the care provider and the service provider. FIG. 2 is a block diagram illustrating a computer network environment 200 suitable for carrying out one or more embodiments disclosed herein. The computer network environment 200 may include a computer network 202. The computer network 202 may take various forms. In some embodiments, the computer network may be a wide area network such as the Internet, for example. The computer network 202 may also be a private network which joins various network nodes. The computer network 202 may also be a local area network in which communication takes place protected from a larger external network such as the Internet, for example. Alternatively, the computer network 202 may be some combination of private and public networks and also of wide area networks and local area networks.

The computer network environment 200 also includes a care provider system 204. The care provider system 204 generally includes various computing devices (described in further detail in FIG. 3 below) which may be used by the care provider to deliver medical care to patients. The care provider system 204 may be connected to the network 202 so that it can communicate information such as medical imaging data, for example, to other entities connected to the network. The care provider system 204 may be protected through various security protocols and devices, including firewalls and other network security apparatuses. The care provider system 204 may further include components and/or devices which are not connected to the computer network 202.

The computer network environment 200 also may include a service provider system 208. As will be discussed in additional detail below in connection with FIG. 4, the service provider system may include one or more computing devices which enable a service provider to provide services relating to patient-specific medical treatment. Like the care provider system 204, the service provider system 208 may include several different types of computing systems which can be used for designing, manufacturing, and/or selecting patient-specific medical devices for use in patient-specific medical treatment. The service provider system 208 may include certain components which are connected to the computer network 202, and it may include certain components which are not. Moreover, the service provider system may also be protected from intrusion via the network 202 using various network security apparatuses and appliances.

The computer network environment 200 also may include an automated segmentation portal 206. The automated segmentation portal 206, which will be discussed in further detail below in connection with FIG. 5, may form part of a distributed system which provides automatic segmentation and default planning services. In various embodiments, the automated segmentation portal may be generally configured to receive medical image data from a care provider, or more particularly from the care provider system 208. The automatic segmentation portal 206 may process the received image data by performing an automatic segmentation and default planning for delivery of patient-specific medical care. The automated segmentation portal 206 generally takes the form of a web-based service which uses server-side or cloud-based application technologies. However, a skilled artisan will appreciate that the automated segmentation portal 206 may reside in the same location on the network 202 as either the service provider system 208 or the care provider system 204. In those implementations, access to the automated segmentation portal 206 may be managed by one or both of the service provider and the care provider.

Figure 3:
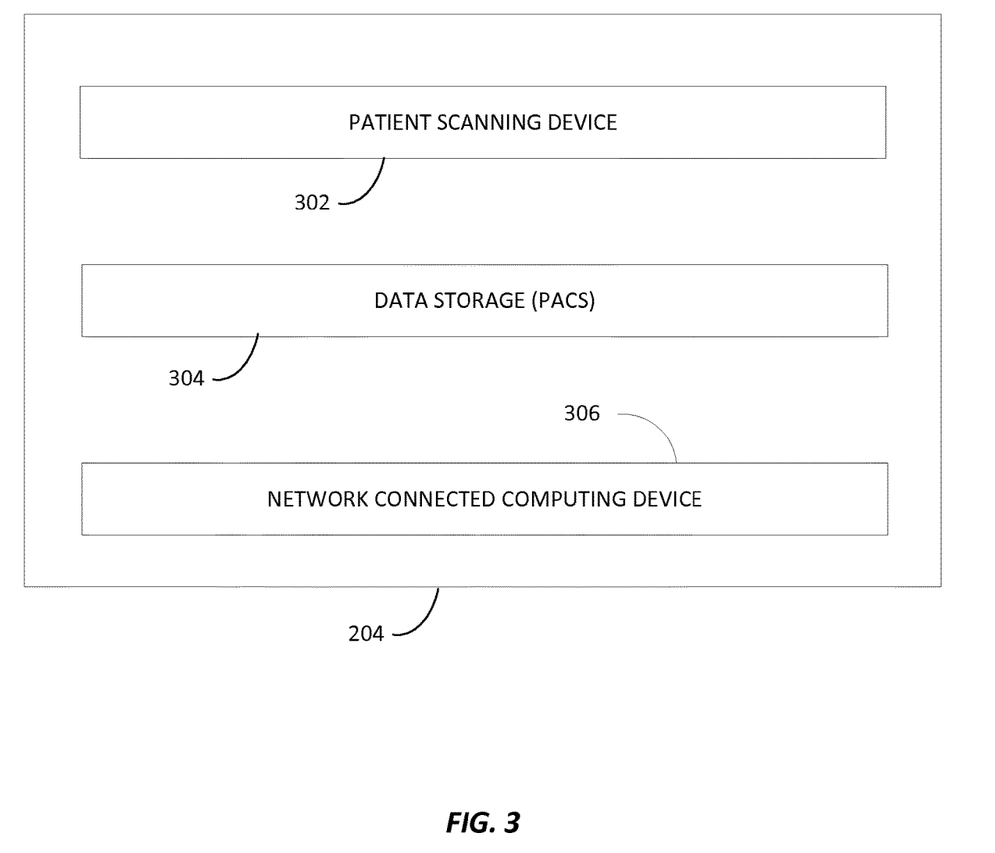
FIG. 3 is a more detailed view of the care provider system shown in FIG. 2.

FIG. 3 is a more detailed view of the care provider system 204 shown in FIG. 2. As shown, the care provider system 204 may include a patient scanning device 302. The patient scanning device 302 may be any of various types of patient scanning devices including an MRI device, a CT scanner, an x-ray scanner, an ultrasound machine, or some other device which can capture images of patient anatomy. The patient scanning device 302 may be operably coupled to and/or in data communication with data storage 304. The data storage 304 may be integrated into the patient scanning device 302. Alternatively, the data storage may take the form of a picture archiving and communication system ("PACS") which provides efficient storage and access to images from multiple modalities. Using the patient scanning device 302, the care provider obtains images of the relevant patient anatomy and may store those images in the data storage 304.

The care provider system 204 also may include one or more network-connected computing devices 306. These network-connected computing devices 306 may be integrated into either or both of the patient scanning device 302 and the data storage 304. Alternatively, the network-connected computing devices 306 may also be separate devices which are in data communication with the patient scanning device 302 and/or the data storage 304. The network-connected computing device 306 may be connected to the computer network 202. Using the network-connected computing device 306, the care provider can retrieve image data from the data storage 304 and then transmit the image data to the automated segmentation portal 206.

Figure 4:
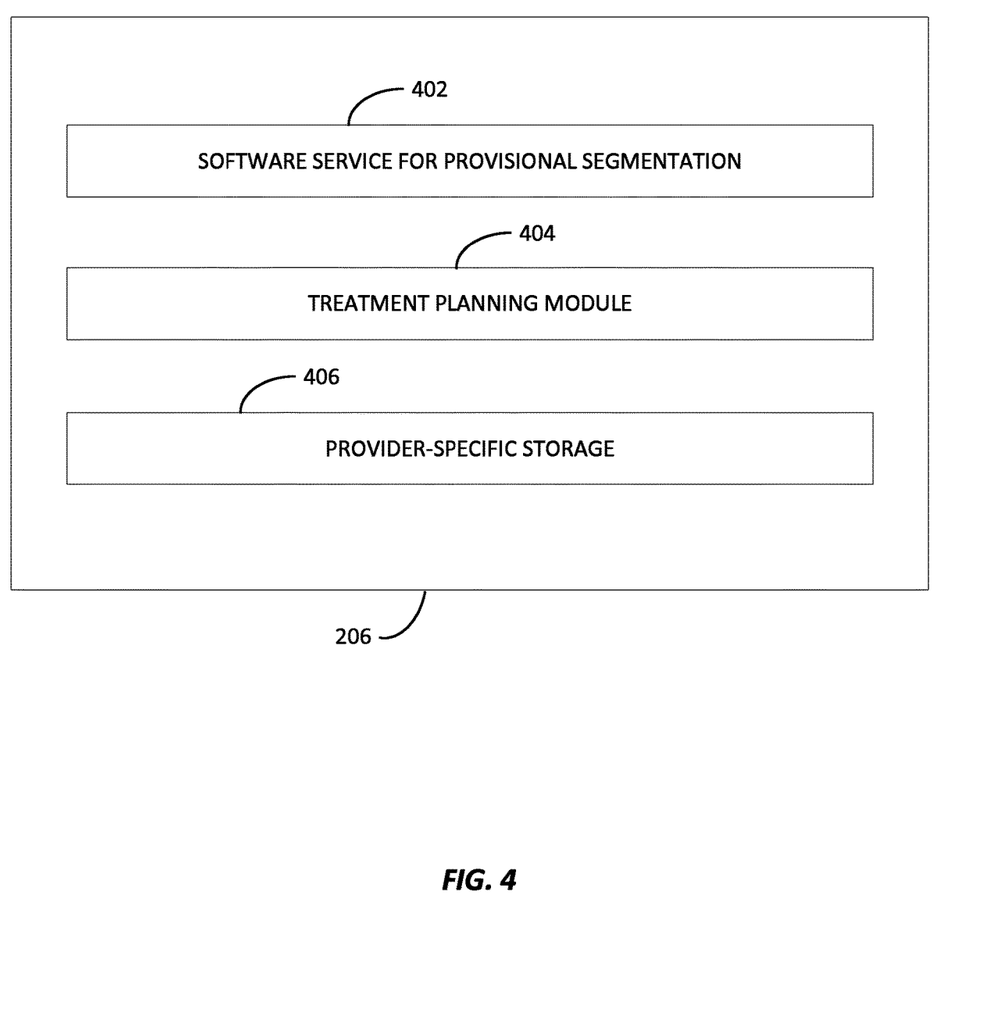
FIG. 4 is a more detailed view of the automated segmentation portal shown in FIG. 2.

FIG. 4 is a more detailed view of the automated segmentation portal 206 shown in FIG. 2. As noted above, the automated segmentation portal 206 may take the form of a software service executed on a network-based server which is accessible via the computer network 202. The automated segmentation portal 206 may include a software service 402 which is utilized to provide provisional segmentation of medical images received by the automated segmentation portal 206. The provisional segmentation service 402 may be configured to receive image data uploaded into provider-specific storage 406 and perform an automatic segmentation of the medical image data which requires minimal user interaction and minimal waiting time. Generally, the provisional segmentation software service 402 can perform an image segmentation in under ten minutes, in many cases under five minutes, and in some cases under two minutes.

The automatic segmentation performed by the provisional segmentation service 402 may be accomplished using various automated segmentation techniques. In one embodiment, the automatic segmentation may rely on thresholding the gray value data in the received medical images. In other embodiments, morphing technology may be utilized. In yet other embodiments, active shape models may be used to create the 3D model. In still other embodiments, active appearance models may be used. In some embodiments, the automated segmentation may be performed by imaging at least the relevant anatomy to create a plurality of 2D image slices. The image slices may be taken orthogonal to an axis extending through the patient's anatomy, where each of the image slices includes a separate bone segment. The bone segment may visible in the image slice as an enclosed boundary which shows the outline of the patient's bone. The bone segment information may be combined with non-patient-specific statistical atlases to extract bone boundaries, and cartilage interfaces. The combined information may then be outputted as a 3D model of the patient's bone.

In general, the automatic segmentation methods do not produce the model with a degree of accuracy that is sufficient for the final design of patient-specific devices that fit and/or conform to the anatomy of the patient. For example, with respect to the technique of using the gray value data, noise or visual artifacts can cause in accuracies and other defects in the output. Similarly, using statistical atlases can also be unreliable because patient-specific features such as osteophytes and local cartilage damage typically cannot be modeled using statistics gathered from the generalized patient population. However, while the quality and accuracy of this automatic segmentation may not be sufficient for the actual design of patient-specific devices, it provides sufficient quality such that the treatment planning module 404 may be used to create a preliminary or default treatment plan for the care provider to review and approve.

Thus, when the automatic image segmentation has been completed, the treatment planning module 404 may use the 3D model generated by the image segmentation to develop a default surgical plan for the patient-specific medical treatment. The plan may be stored in the provider-specific storage 406, or it may be returned immediately to the care provider for evaluation and plan approval. The care provider may modify or adjust the plan using the treatment planning module 404. In some instances, the plan may include preliminary device designs. Those designs may also be modifiable by the care provider using the treatment planning module 404. Advantageously, the software service 402 and the treatment planning module 404 may perform the segmentation and planning procedure in a matter of minutes. Because the preliminary segmentation and planning is performed quickly, it allows for the care provider to achieve plan approval in a matter of minutes rather than days.

As noted above, the automated segmentation portal 206 may also include provider-specific storage 406. The provider-specific storage 406 may take the form of server-based storage which is segmented into care provider-specific storage areas, each accessible only by specific, authorized care providers. Thus, the automated segmentation portal 206 may be made available to many different care providers in such a way that patient data and other care provider-specific information remains sufficiently secure and confidential.

Although the automated segmentation portal 206 is described as a web-based service accessible to the care provider via the network-connected computing device 306 within the care provider system 204, it is to be appreciated that the software service for provisional segmentation 402 in the treatment planning module 404 could be implemented as a client-side application at the care provider site. However, because many medical care institutions have strict software security policies, a client-site implementation may not be as practical in many cases. Utilizing a cloud-based solution such as that described in connection with FIG. 4, the care provider typically will not require any additional software on the network-connected computing device 306. Rather the automated segmentation portal 206 can be accessed using a standard web browser.

In some embodiments, the automated segmentation portal 206 may allow for use cases that engender even more efficient use of care provider resources. For example, in some embodiments the automated segmentation portal 206 may be configured to permit members of the care provider staff (other than the treating physician or surgeon) to upload the image data for patients and initiate the automated segmentation and treatment planning process. In these implementations, an assistant, a nurse, or some other employee at the care provider site can be authorized to upload image data for a plurality of cases. Each of these cases can be segmented by the software service 402 and a treatment plan can be generated by the treatment planning module 404 and stored in the provider-specific storage 406. Once all of the cases have been stored, the surgeon or physician associated with the care provider can consult, review, and approve the treatment plans all at once. This process allows the surgeon to address groups of cases at his or her convenience, rather than having to carve out time in his or her schedule to deal with each case individually.

When the default treatment plan has been approved on the automated segmentation portal 206, all of the case data can, at that point, be made available to the service provider. This case data may include medical images, the automated segmentation, the approved treatment plan, and possibly additional case-specific information. Using the case data, the service provider can manually fine-tune the automated segmentation to improve the quality and accuracy of the segmentation so that it is of sufficient quality and accuracy for patient-specific device design. In some embodiments, the service provider, rather than using a manual segmentation process, may utilize a computationally-intensive automatic segmentation method to achieve the needed quality and accuracy. This computationally-intensive automatic segmentation method would typically not be suitable for use in the automated segmentation portal 206, because the time required to perform the computationally-intensive technique would be too long to allow for the care provider to upload the image data and approve a default treatment plan in a single session.

Figure 5:
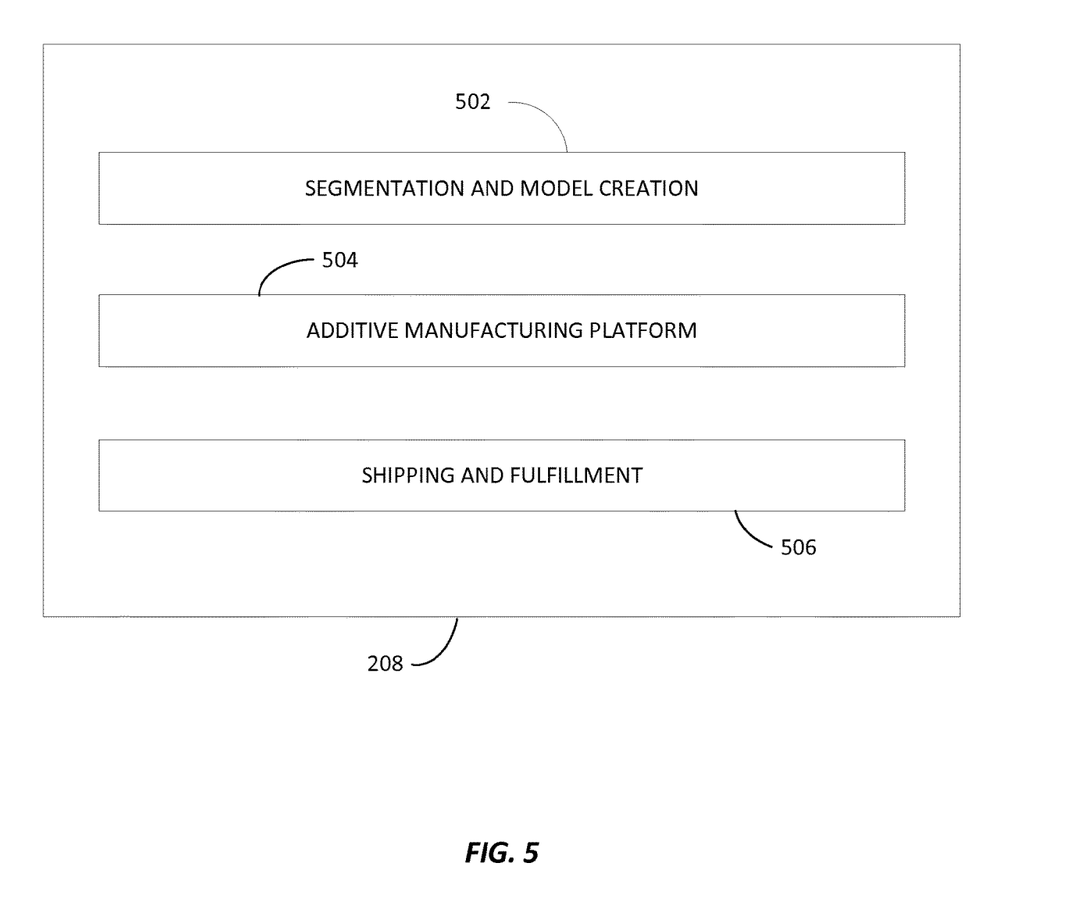
FIG. 5 is a more detailed view of the service provider system shown in FIG. 2.

Turning now to FIG. 5, a more detailed view of the service provider system shown in FIG. 2 is provided. As noted previously, the service provider system 208 generally takes the form of a group of computing devices and manufacturing platforms which allow the service provider to perform high quality segmentation, device design, manufacturing, and fulfillment. As shown, the service provider system 208 may include a segmentation and model creation software 502. The segmentation and model creation software may be operated on a general-purpose computing device such as a personal computer or tablet. The segmentation and model creation software 502 generally allows the service provider to generate a 3-D model with sufficient quality and accuracy to allow for the design of a patient-specific medical device for use in delivering patient-specific medical treatment. This software 502 may be commercial off-the-shelf software such as the Mimics Innovation Suite from Materialise N.V. (Leuven, Belgium), for example. Alternatively, the segmentation and model creation software 502 may be customized and proprietary image segmentation and 3-D model creation software.

The service provider system 208 also may include an additive manufacturing platform 504. The additive manufacturing platform 504 may be used to manufacture patient-specific medical devices and patient-specific medical instruments which may be used to deliver patient-specific medical care by the care provider. The additive manufacturing platform 504 typically includes a 3-D printer, a control computer, and control software configured to receive a 3-D object design which is used to manufacture the object using the 3-D printer. The 3-D printer may be anyone of various known 3-D printing technologies, including but not limited to stereolithography, selective laser sintering, selective laser melting, fused deposition modeling, or some other 3-D printing technology. The service provider system 208 may further include a shipping and fulfillment function 506. The shipping fulfillment function 506 generally allows the appropriate devices needed by the surgical plan to be shipped to the care provider so that they may be utilized in delivering patient-specific medical treatment.

Advantageously, utilizing the system described in connection with FIGS. 2-5, the service provider is able to set up an operational arrangement that does not depend on a timely response from the care provider in approving surgical planning. It is only after the default plan has been approved by the care provider that a case is sent to the service provider. And at the time the information is received, the service provider generally has all of the information needed to design, manufacture, select, and ship the necessary devices to the care provider. Moreover, by eliminating the feedback loops present in conventional patient-specific medical treatment, the service provider is much better positioned to implement effective capacity planning and to achieve improved lead times for the manufacture of patient-specific medical devices.

Figure 6:
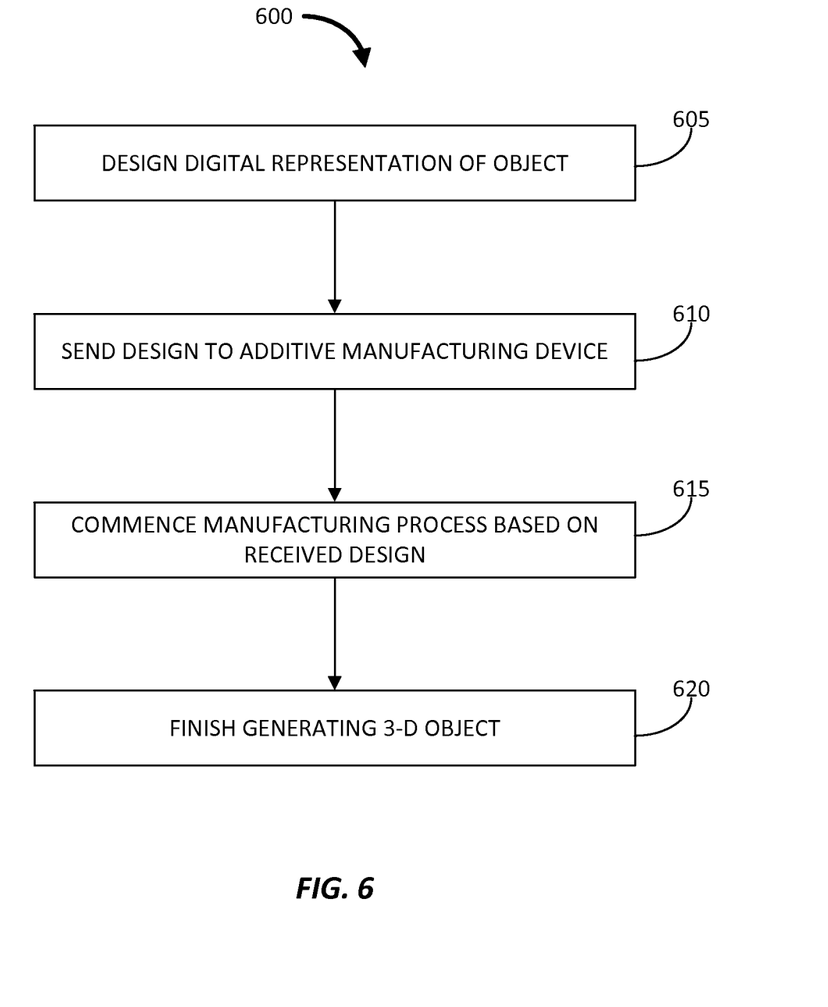
FIG. 6 depicts a general process flow of manufacturing a medical treatment device using additive manufacturing technology.

As discussed above, patient-specific devices may be manufactured using 3-D printers and additive manufacturing technologies more generally. FIG. 6 depicts the process flow for creating a medical treatment using the device using additive manufacturing technology. As shown, at block 605, a digital representation of the object is designed, for example, 3-D modeling software. For example, 2-D or 3-D data (such as the segmented images created by the software 502) may be used to design the digital representation of the 3-D object. Continuing at block 610, information to an additive manufacturing device, such as one which is part of additive manufacturing device 504, and the additive manufacturing device commences the manufacturing process in accordance with the received information. At block 615, the additive manufacturing device continues manufacturing the 3-D object using suitable materials, such as a liquid resin (for stereolithography applications, for example), powder (for sintering applications), thermoplastic (for fused deposition modelling), or some other suitable 3-D printing material. Further, at step 620, the 3-D object is generated. These suitable materials may include, but are not limited to a photopolymer resin, polyurethane, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESDI, ABS-M30, ABS-M30i, PC-ABS, PC ISO, PC, ULTEM 9085, PPSF and PPSU materials from Stratasys;

Accura Plastic, DuraForm, CastForm, Laserform and VisiJet line of materials from 3D-Systems; the PA line of materials, PrimeCast and PrimePart materials and Alumide and CarbonMide from EOS GmbH. The VisiJet line of materials from 3-Systems may include Visijet Flex, Visijet Tough, Visijet Clear, Visijet HiTemp, Visijet e-stone, Visijet Black, Visijet Jewel, Visijet FTI, etc. Examples of other materials may include Objet materials, such as Objet Fullcure, Objet Veroclear, Objet Digital Materials, Objet Duruswhite, Objet Tangoblack, Objet Tangoplus, Objet Tangoblackplus, etc. Another example of materials may include materials from the Renshape 5000 and 7800 series.

Figure 7:
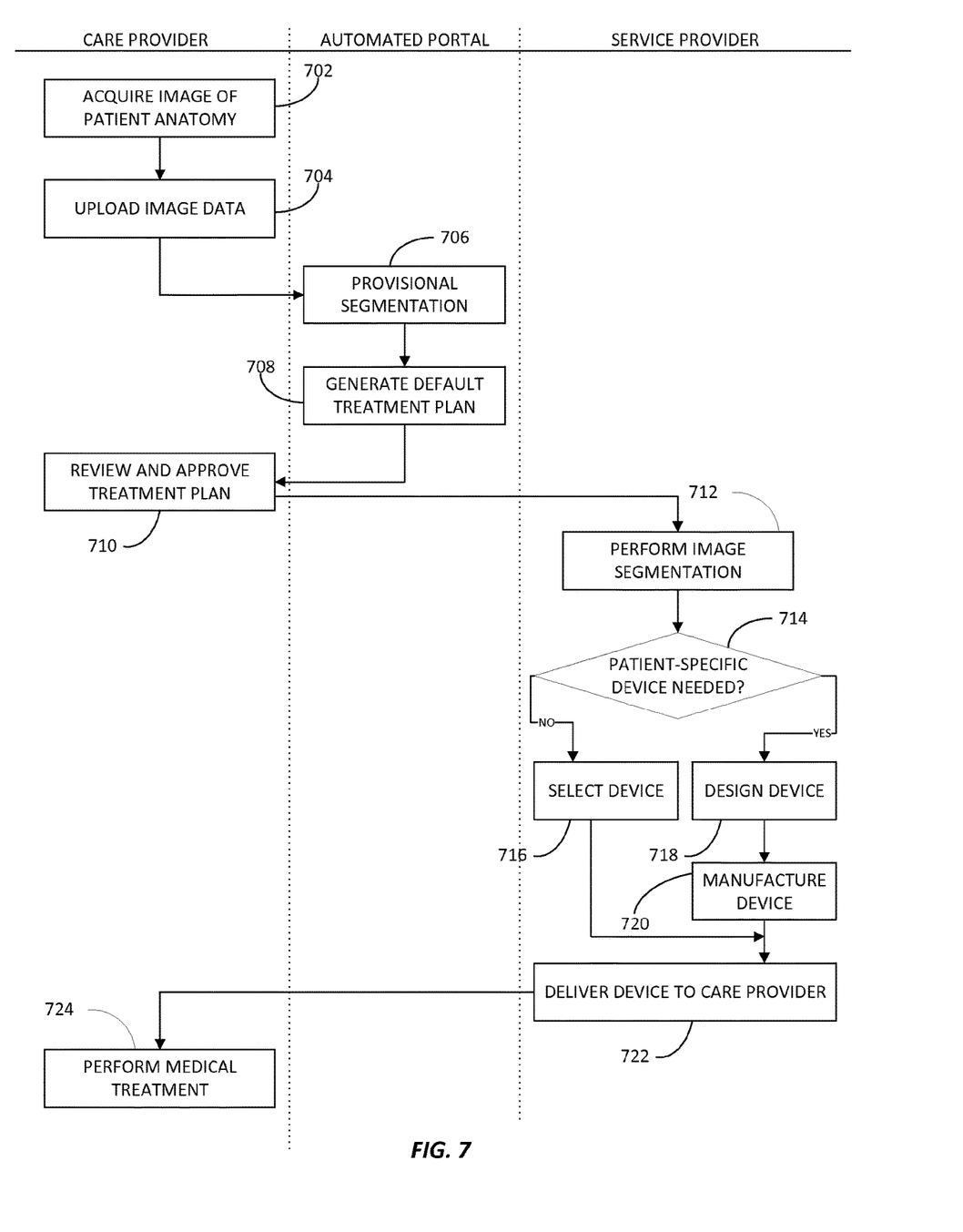
FIG. 7 is a flow chart illustrating a method for planning a patient-specific medical treatment according to one or more embodiments.

Using an additive manufacturing process (such as the process described in connection with FIG. 6) in combination with the systems described in connection with FIGS. 2-5, a patient-specific medical device or instrument may be efficiently and quickly designed, manufactured, and delivered for use in delivering patient-specific medical treatment. However, a skilled artisan will appreciate that these configurations are merely examples, and that other types of systems and configurations may be used to perform inventive methods as disclosed herein. Turning now to FIG. 7, a flow chart illustrating a method of planning a patient-specific medical treatment according to one or more embodiments is provided. In the flow chart, the various steps are positioned vertically in one of three columns based on the party or entity carrying out that particular step. Although FIG. 7 provides one illustration of the parties performing each step, is to be appreciated that in certain embodiments, certain steps may be performed by an entity other than the entity shown in FIG. 7.

The process begins at block 702 where the care provider acquires images of the relevant patient anatomy. As discussed above, the acquisition of images may be performed by a patient scanning device such as patient scanning device 302 and those images may be stored in data storage such as, for example data stores 304. Next, the process moves to block 704 where the acquired image data is uploaded for segmentation. The upload may be performed by a network-connected computing device such as computing device 306 described above in connection with FIG. 3. The process then moves to block 706. There a provisional segmentation is performed on the uploaded image data, and then at block 708 a default treatment plan is generated. As shown, this provisional segmentation and default planning may be performed by the automated segmentation portal 206 operating as a network service accessible via an Internet browser. But, as discussed above, the provisional segmentation and default planning may also be performed by locally installed computer software that resides with the care provider.

Next, the process moves to block 710, where the care provider reviews and approves the treatment plan. When the treatment plan has been approved the process moves to block 712, where the service provider receives the relevant data such as the medical images, the approved planning, etc., and performs a segmentation that has sufficient quality and accuracy to utilize for designing a patient-specific medical device. Next, the process moves to decision block 714. There, the service provider determines whether or not a patient-specific device is needed to carry out the approved treatment plan. In some cases, the patient anatomy and/or pathology may be such that the patient-specific devices are not needed, and instead and off-the-shelf device may be selected from a library of implants that have different shapes and/or sizes to best match the patient's anatomy or pathology. If the service provider determines that a patient-specific device is not needed, the process moves to block 716 where an off-the-shelf device is selected and then delivered to the care provider at block 722. If the service provider determines at decision block 714 that a patient-specific device is required by the surgical plan, the process moves to block 718 where the patient-specific device is designed. Next, the process moves to block 720, where the designed device is manufactured according to the design, and then delivered to the care provider at block 722. Once the device has been delivered to the care provider, the process moves to block 724, where the care provider performs the patient-specific medical treatment according to the surgical plan.

Figure 8:
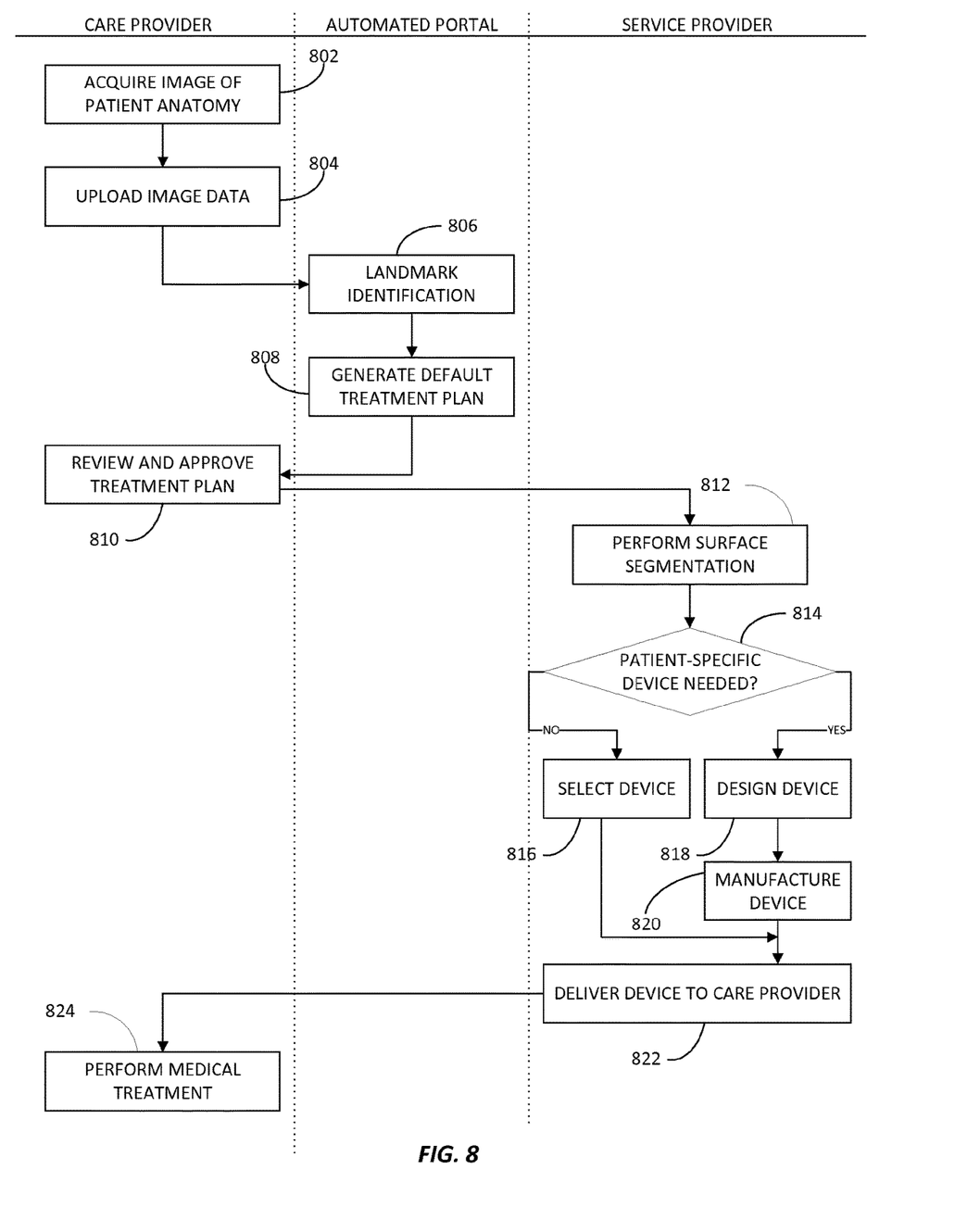
FIG. 8 is a flow chart illustrating another method for planning a patient-specific medical treatment according to one or more embodiments.

In some embodiments, instead of providing a full 3-D model of the anatomy of the patient, the automatic segmentation performed by the automated segmentation portal 206 may be limited to an identification of certain anatomical landmark points that are needed for creating a default treatment plan. For example, these landmark points could be utilized in a total knee arthroplasty ("TKA") procedure. In the TKA procedure, landmark points could be the hip point, both malleoli of the ankle, the epicondyles of the femur, the most anterior point of the distal femur, the most posterior points of both condyles, the tibia spine points, the most distal points of the tibial plateaus, the posterior notch of the tibia, the tuberosity of the tibia, or some other points in the patient anatomy. In these embodiments, visualization may be done using volume rendering. FIG. 8 is a flow chart illustrating a process by which a default treatment plan may be created according to this embodiment.

The process begins at block 802 where the care provider acquires the image of the relevant patient anatomy. The process next moves to block 804 where the acquired image data is uploaded to the automated segmentation portal for processing. The process continues at block 806 where landmark identification takes place, and based on the identified anatomical landmark points a default treatment plan is generated at block 808. Next, the process moves to block 810 where the care provider reviews and approves the generated treatment plan, and the relevant case information is sent to the service provider. At block 812, the service provider performs surface segmentation on the received image data, and then the process moves to decision block 814, where the service provider determines whether the approved plan requires a patient-specific device. If not, the process moves to block 816 where an off-the-shelf device is selected from a device library, and that selected devices delivered to the care provider block 822. If, at decision block 814, it is determined that a patient-specific device is necessary to carry out the plan, the process instead moves to block 818 where the patient-specific devices designed and then to block 820 where the designed device is manufactured. Once the device has been manufactured the process moves to block 822, where the manufactured devices delivered to the care provider. The process ends at block 824 where the care provider delivers the patient-specific medical treatment using the device received from the service provider.

Various embodiments disclosed herein involve the use of computers and computer control systems. A skilled artisan will readily appreciate that these embodiments may be implemented using numerous different types of computing devices, including both general purpose and/or special purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general purpose single- or multi-chip microprocessor such as a Pentium® processor, a Pentium® Pro processor, an 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or nontransitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A method of delivering a patient-specific medical treatment to a patient, the method comprising:
    acquiring image data of a patient anatomy;
    uploading the image data to an automated segmentation portal;
    receiving a default treatment plan from the automated segmentation portal, wherein the default treatment plan is generated based on a first 3D model of the patient anatomy that is generated based on a first segmentation of the image data performed by the automated segmentation portal;
    approving the generated treatment plan;
    transmitting the approved treatment plan to a service provider;
    receiving a medical device from the service provider, wherein the medical device comprises at least one of a patient-matched medical device selected from a device library or a manufactured patient-specific medical device, wherein the medical device is based on the approved treatment plan and a second 3D model of the patient anatomy that is generated based on a second segmentation of the image data, the second segmentation of the image data being more accurate than the first segmentation of the image data, and the second 3D model being more accurate than the first 3D model, wherein the first 3D model of the patient anatomy and the first segmentation are not accurate enough to design the medical device as a patient-specific device, and wherein the second 3D model of the patient anatomy and the second segmentation are accurate enough to design the medical device as a patient-specific device; and
    delivering the patient-specific treatment to the patient using the received medical device.

2. The method of claim 1, wherein the manufactured patient-specific medical device is manufactured using additive manufacturing.

3. The method of claim 2, wherein the first segmentation of the image data comprises an automatic segmentation.

4. The method of claim 3, wherein the second segmentation comprises a manual segmentation.

5. The method of claim 3, wherein the automatic segmentation comprises thresholding grey value data in the image data.

6. The method of claim 3, wherein the automatic segmentation comprises a statistical information-based segmentation technique.

7. The method of claim 3, wherein the default treatment plan is generated in less than 10 minutes after the image data is uploaded to the automated segmentation portal.

8. The method of claim 3, wherein the automatic segmentation lacks quality needed to design a patient-specific device.

9. The method of claim 3, wherein the automatic segmentation is limited to an identification of anatomical landmark points.

10. The method of claim 9, wherein the patient-specific medical treatment is a total knee arthroplasty.

11. The method of claim 10, wherein the anatomical landmark points comprise four or more of a hip point, malleoli of an ankle, epicondyles of a femur, a most anterior point of a distal femur, a most posterior point of a condyle, a tibia spine point, a most distal point of a tibial plateau, a posterior notch of a tibia, and a tuberosity of the tibia.

12. The method of claim 11, wherein the patient anatomy is visualized using volume rendering.

13. The method of claim 4, wherein the manual segmentation comprises fine-tuning the automatic segmentation.

14. The method of claim 13, wherein the transmitting the approved treatment plan to the service provider comprises an initial transmission of data to the service provider relating to the patient-specific medical treatment.

15. The method of claim 1, further comprising reviewing and editing the generated treatment plan prior to approving the plan.

16. The method of claim 15, wherein the generated treatment plan includes a preliminary design for a patient-specific instrument, and wherein editing the generated treatment plan comprises making adjustments to the shape of the patient-specific instrument.

17. The method of claim 16, wherein the service provider modifies the approved patient-specific instrument to improve its engagement with a contact surface of the patient anatomy.

18. A method of delivering a patient-specific medical treatment to a patient, the method comprising:
    acquiring image data of a patient anatomy;
    uploading the image data to an automated segmentation portal;
    receiving a default treatment plan from the automated segmentation portal, wherein the default treatment plan is generated based on a first 3D model of the patient anatomy that is generated based on a first segmentation of the image data performed by the automated segmentation portal;

approving the generated treatment plan;

transmitting the approved treatment plan to a service provider;

receiving a medical device from the service provider, wherein the medical device comprises at least one of a patient-matched medical device selected from a device library or a manufactured patient-specific medical device, wherein the medical device is based on the approved treatment plan and a second 3D model of the patient anatomy that is generated based on a second segmentation of the image data, the second segmentation of the image data being more accurate than the first segmentation of the image data, and the second 3D model being more accurate than the first 3D model, wherein the first 3D model of the patient anatomy and the first segmentation are not accurate enough to design the medical device as a patient-specific device, and wherein the second 3D model of the patient anatomy and the second segmentation are accurate enough to design the medical device as a patient-specific device; and delivering the patient-specific treatment to the patient using the received medical device.

\* \* \* \* \*